United States Patent [19]

Kohama et al.

[11] Patent Number: 4,834,977
[45] Date of Patent: May 30, 1989

[54] POISON BAIT FOR CONTROL OF NOXIOUS INSECTS

[75] Inventors: Takuji Kohama; Fumiyasu Minagawa; Goro Shinjo, all of Toyonaka; Shigenori Tsuda, Kyoto; Kazuyuki Maeda, Nishinomiya, all of Japan

[73] Assignee: Sumitomo Chemical Company, Limited, Osaka, Japan

[21] Appl. No.: 164,200

[22] Filed: Mar. 4, 1988

[30] Foreign Application Priority Data

Mar. 6, 1987 [JP] Japan ................................. 62-52498

[51] Int. Cl.⁴ ............................................. A61K 25/60
[52] U.S. Cl. ....................................... 424/405; 424/84
[58] Field of Search ................... 424/405, 409, 410, 84

[56] References Cited

U.S. PATENT DOCUMENTS

| 4,007,258 | 2/1977 | Cohen et al. | 424/409 |
| 4,277,364 | 7/1981 | Shaska et al. | 424/487 |
| 4,344,857 | 8/1982 | Shaska et al. | 424/418 |
| 4,563,344 | 1/1986 | Kotz et al. | 424/410 |
| 4,696,822 | 9/1987 | Matsumino | 424/496 |
| 4,732,762 | 3/1988 | Sjogren | 424/409 |

OTHER PUBLICATIONS

11th Revisions Commentary for Japanese Pharmacopeia C–1475 (1986).
Jap. J. Saint. Zool., 20 (4) 240 (1969).
Japanese Patent Publication (unexamined) No. 144304/1983.

Primary Examiner—Thurman K. Page
Assistant Examiner—L. R. Horne
Attorney, Agent, or Firm—Birch, Stewart, Kolasch & Birch

[57] ABSTRACT

A composition which includes (a) at least one insecticide selected from the group consisting of organic phosphorous insecticides, carbamate insecticides and pyrethroid insecticides in a microencapsulated form, (b) crystalline cellulose and (c) crop product powders, which is useful as a bait for control of noxious insects.

13 Claims, No Drawings

POISON BAIT FOR CONTROL OF NOXIOUS INSECTS

This invention pertains to a poison bait for control of noxious insects, particularly cockroaches.

There have heretofore been commercially available some powdery poison baits for exterminating noxious insects such as cockroaches. These conventional powdery poison baits are however practically disadvantageous and dangerous in causing many problems from the standpoints of sanitary and daily use. For instance, they adhere to the hands on handling, continue to contaminate the surroundings even after being situated in desired places, or are erroneously consumed as food by infants and house animals.

In order to solve the above problems, a poison bait in a tablet form was put into the market, which comprises boric acid as the active ingredient. For assurance of the exterminating effect, however, these poison bait tablets contain boric acid in such a large amount as about 20 to 30% by weight. For this reason, they are still not safe for infants and house animals. In fact, it is reported that even a nursery powder containing boric acid in an amount of only 5% by weight accidentally produced the death of an infant (11th Japan Pharmacopoeia, C-1475 (1986)). In addition, the exterminating effect of boric acid against cockroaches is exerted quite belatedly, and it takes usually one week or more after feeding until their death, during which they are attacked by diarrhea and produce soft excrements so that their habitats and surroundings are considerably stained thereby.

There are also known some poison baits in tablets, which comprise as the active ingredient an insecticide chosen from organic phosphorus insecticides, carbamate insecticides, pyrethroid insecticides, etc. Since those insecticides have a much higher insecticidal potency than boric acid, their content in poison baits may be much smaller, so that the resulting poison baits are considerably safer. However, these insecticides each have a characteristic odor, and a tablet preparation comprising the same is likely to be refused by cockroaches. Thus, the feed attractant effect is deteriorated significantly, naturally the exterminating effect is lowered. Further, organic phosphorous insecticides or carbamate insecticides can be readily hydrolyzed even with the slightest amount of water to produce a certain specific odor so that the feed attractant effect is likewise deteriorated and the exterminating effect is decreased. The hydrolysis results in a lowering of the content of the active ingredient itself, and the insecticidal effect is thus remarkably deteriorated.

As a result of an extensive study to overcome the drawbacks as seen in conventional poison baits for noxious insects including cockroaches, there is now provided a poison bait composition in a shaped form which comprises (a) at least one insecticide selected from the group consisting of organic phosphorus insecticides, carbamate insecticides and pyrethroid insecticides in a microencapsulated form and (b) crystalline cellulose and (c) crop product powders as the essential components. In such composition, the essential components (a), (b) and (c) may be contained respectively in amounts of about 0.05 to 5.0% by weight, about 20.0 to 60.0% by weight and about 11.3 to 79.0% by weight on the total weight of the composition.

The insecticide as the component (a) may be chosen from organic phosphorus insecticides, carbamate insecticides and pyrethroid insecticides. As the organic phosphorus insecticides, there are exemplified calbinphos, chlorpyriphos, chlorpyriphosmethyl, cyanofenphos, cyanophos, diazinon, dichlorvos, fenitrothion, fenthion, malathion, naled, pirimiphosmethyl, prothiophos, pyridaphenthion, salithion, tetrachlorvinphos, trichlorfon, bromophos, propetamphos, etc. Examples of the carbamate insecticides are BPMC, carbaryl, CPMC, ethiofencarb, MPMC, MTMC, promecarb, swep, propoxur, etc. Examples of the pyrethroid insecticides are cypermethrin, cyphenothrin, deltamethrin, fenpropathrin, fenvalerate, kadethrin, permethrin, phenothrin, proparthrin, resmethrin, ethofenprox, cyfluthrin, alphamethrin, tralomethrin, fulcythrinate, etc. Their geometrical or optical isomers may be also used. The content of the insecticide may vary within a wide range depending upon the individual insecticide as used, the species of the insect to be treated, etc. Usually, it may be within a range of about 0.05 to 5.0% by weight to the total weight of the composition.

For the use in this invention, the insecticide is microencapsulated by a per se conventional procedure using any film-forming material. The film-forming material may be any one which can form a film having a strength tolerable to the impact which may be applied thereto at a later stage, i.e. the stage of shaping. Examples of the film-forming material are formalin-urea resin, polystyrene, polyvinyl acetate, polyacrylonitrile, polyethylene, polybutyl methacrylate, polyisobutylene, polybutadiene, gelatin, casein, albumin, fibrinogen, polyvinyl pyrrolidon, carrageenan, sodium alginate, agar, gum arabic, tragacanth gum, locust bean gum, guar gum, carboxymethyl cellulose, polyvinyl sulfonate, cellulose derivatives, polyvinly derivatives, starch derivatives, vinylpyridine-acrylic acid copolymer, silicic acid, polyurea, polyurethane, polyamides, polyesters, polycarbonates, polysulfonates, polysulfonamides, epoxy resins, etc.

The component (b) is crystalline cellulose, of which a typical example is "Avicel ®" (Asahi Chemical Industry Co., Ltd.). It may be normally used in an amount of about 20.0 to 60.0% by weight to the total weight of the bait composition.

As the component (C), there are used crop product powders such as potato starch, sweet potato starch, corn starch, wheat flour, rice powder and corn powder. Its amount is usually from about 11.3 to 79.0% by weight on the basis of the total weight of the bait composition.

In addition to the essential components, the bait composition of the invention may comprise a saccharide such as sucrose, glucose, fructose, lactose, black sugar, brown sugar or soft brown sugar, usually in an amount of about 1.0 to 40.0% by weight on the basis of the total weight of the bait composition for enhancement of the feeding effect.

When desired, the bait composition may further comprise an additive(s) and/or an auxiliary agent(s), particularly an anti-oxidizing agent, a preservative, a mis-feed inhibitor, a flavoring agent, a feed attractant, etc. Examples of the anti-oxidizing agent are erythorbic acid, sodium erythorbate, dibutyl hydroxytoluene, dl-alpha-tocophelol, nordihydroguaiaretic acid, methylhydroxyanisole, propyl gallate, guaiac resin, L-cysteine hydrochloride, etc. Examples of the preservative are benzoic acid, sodium benzoate, salicylic acid, diphenyl, sorbic acid, potassium sorbate, dehydroacetic acid, sodium dehydroacetate, isobutyl p-oxybenzoate, isopropyl p- oxybenzoate, ethyl p-oxybenzoate, butyl p-oxybenzoate, propyl p-oxybenzoate, calcium propionate, sodium propionate, etc. As the mis-feed inhibitor, there may be exemplified red pepper powders, Amaranth, Amaranth aluminium lake, Erythrosine, Erythrosine aluminium lake, New Coccine, Phloxine, Rose Bengal, Acid Red, Tartrazine, Tartrazine aluminium lake, Sunset Yellow FCF, Sunset Yellow FCF aluminium lake, Fast Green FCF, Fast Green FCF aluminium lake, Brilliant Blue FCF, Brilliant Blue FCF aluminium lake, Indigo Carmine, Indigo Carmine aluminium lake, beta-carotene, copper chlorophyll, etc. Examples of the flavoring agent are cheese flavor, butter flavor, peanut flavor, peach flavor, strawberry flavor, milk flavor, etc. Examples of the feed attractant are essential oils such as soybean oil, rapeseed oil, sesame oil, cotton seed oil, wheat germ oil, corn oil, sunflower oil, palm oil, castor oil and linseed oil.

According to the invention, a mixture of the above mentioned essential and optional components may be prepared into an appropriately shaped form, preferably tablets, by a per se conventional procedure to obtain a bait composition. For instance, one or more insecticides as microencapsulated by a per se conventional procedure are mixed with crystalline cellulose, crop product powders and optionally other components to make a uniform mixture, which is then tabletted by a per se conventional procedure to produce a bait composition in a tablet form. When two or more insecticides are used, each of them or a mixture of them may be microencapsulated; if necessary, two or more insecticides may be each microencapsulated and combined together, followed by microencapsulation of the resultant mixture.

The thus obtained bait composition exerts a remarkable insecticidal effect against a wide range of harmful insects, of which examples are cockroaches (Blattidae) such as *Periplaneta americana*, *Blattella germanica* and *Periplaneta fuliginosa*, ants (Formicidae) such as *Monomorium pharaonis*, *Monomorium nipponense*, *Lasius fuliginosus* and *Formica japonica*, pillbug (Armadillidae), deathwatch and drugstore beetles (Anobiidae) such as *Lasioderma serricorne* and *Stegobium paniceum*, darkling beetles (Tenebrionidae) such as *Tribolium castaneum* and *Tribolium confusum* and cucujid beetles (Cucujidae) such as *Oryzaephilus surinamensis* and *Cryprolestes pusillus*, etc.

Practical embodiments for preparation of the insecticidal composition according to the invention are illustratively shown in the following Examples wherein part(s) are by weight unless otherwise indicated.

EXAMPLES 1 to 9

Fenitrothion (0.5 part) microencapsulated with polyurethane, crystalline cellulose (30.0 parts) and dehydroacetic acid (0.1 part) were mixed together, and a saccharide (as shown in Table 1) and potato starch (as shown in Table 1) were incorporated therein, followed by mixing uniformly. The resultant mixture was tableted under a compression of 15 kg/cm$^2$ to make tablets, each weighting about 4 g (diameter, about 30 mm).

The thus obtained tablets as a bait were subjected to evaluation of the stability of the active ingredient, the feed attractant effect and the insecticidal effect in the following manner:

(1) Stability of the active ingredient:

The bait in a tablet form was kept at 50° C. for 10 days and subjected to measurement of the remaining percent of the active ingredient by gas chromatography. The bait having a remaining percent of not less than 80% was regarded satisfactory (O), while that having a remaining percent of less than 80% was regarded unsatisfactory (X). The results are shown in Table 1.

(2) Feed attractant effect:

Fifty imagos of *Blattella germanica* (even numbers in male and female) were admitted in a container having a bottom area of 0.12 m$^2$ where the bait in a tablet form as well as a solid bait as control were placed. An attractive rate of the test insect was calculated on the basis of the numbers of the insect attracted within a designated time. The attractant rate of not less than 70% was regarded satisfactory (+), while that of less than 70% was regarded unsatisfactory (−). The results are shonw in Table 1.

(3) Insecticidal effect:

Evaluation of the insecticidal effect was conducted in the same manner as in evaluation of the feed attractant effect, and the lethal rate was observed after continuous feeding for 24 hours. The lethal rate of not less than 80% was regarded satisfactory (+), while that less than 80% was regarded unsatisfactory (−). The results are shown in Table 1.

TABLE 1

| Components | (part(s) by weight) Example | | | | | | | | |
|---|---|---|---|---|---|---|---|---|---|
| | 1 | 2 | 3 | 4 | 5 | 6 | 7 | 8 | 9 |
| Saccharide | | | | | | | | | |
| Black sugar | — | — | 1.0 | — | — | 10.0 | 20.0 | 30.0 | 40.0 |
| Brown sugar | — | 2.0 | — | — | 10.0 | — | — | — | — |
| Soft brown sugar | 5.0 | — | — | 10.0 | — | — | — | — | — |
| Potato starch | 64.4 | 67.4 | 68.4 | 59.4 | 59.4 | 59.4 | 49.4 | 39.4 | 29.4 |
| Stability of active ingredient | O | O | O | O | O | O | O | O | O |
| Feed attractant effect | | | | | | | | | |
| Immediately after tableting | + | + | + | + | + | + | + | + | + |
| After being kept at 50° C. for 10 days | + | + | + | + | + | + | + | + | + |
| Insecticidal effect | | | | | | | | | |
| Immediately after tableting | + | + | + | + | + | + | + | + | + |
| After being kept at 50° C. for 10 days | + | + | + | + | + | + | + | + | + |

EXAMPLES 10 to 13

An insecticide as microencapsulated (as shown in Table 2), crystalline cellulose (30.0 parts) and dehydroacetic acid (0.1 part) were mixed together, and soft brown sugar (5.0 part) and potato starch (as shown in Table 2) were added thereto, followed by mixing uniformly. The resultant mixture was tableted under a compression of 15 kg/cm$^2$ to make tablets, each weighing about 4 g (diameter, about 30 mm). The thus obtained tablets as a bait were subjected to evaluation of the stability of the active ingredient, the feed attractant effect and the insecticidal effect in the same manner as in Example 1. The results are shown in Table 2.

COMPARATIVE EXAMPLES 1 to 4

In the same manner as in Examples 10 to 13 but using the insecticide as not microencapsulated, there were prepared tablets as a bait. Stability, feed attractant effect and insecticidal effect were observed in the same manner as in Examples 10 to 13. The results are shown in Table 2.

It is understood from the above results that the baits comprising the microencapsulated insecticide are much superior to those comprising the non-microencapculated insecticide in stability, feed attractant effect and insecticidal effect.

EXAMPLES 14 to 19

In the same manner as in Example 1, there were prepared, as a bait, tablets comprising the components as shown in Table 3. Stability, feed attractant effect and insecticidal effect were observed in the same manner as in Example 1, of which the results are shown in Table 3.

TABLE 2

| | (part(s) by weight) | | | | | | | |
|---|---|---|---|---|---|---|---|---|
| | Example | | | | Comparative | | | |
| | 10 | 11 | 12 | 13 | 1 | 2 | 3 | 4 |
| Component | | | | | | | | |
| Insecticide | | | | | | | | |
| Fenitrothion | 0.5 | — | — | — | — | — | — | — |
|  | — | — | — | — | 0.5 | — | — | — |
| Cyanophos*1 | — | 0.5 | — | — | — | — | — | — |
|  | — | — | — | — | — | 0.5 | — | — |
| Resmethrin*2 | — | — | 0.3 | — | — | — | — | — |
|  | — | — | — | — | — | — | 0.3 | — |
| BPMC*2 | — | — | — | 0.7 | — | — | — | — |
|  | — | — | — | — | — | — | — | 0.7 |
| Potato starch | 64.4 | 64.4 | 64.6 | 64.2 | 64.4 | 64.4 | 64.6 | 64.2 |
| Evaluation | | | | | | | | |
| Stability of active ingredients | O | O | O | O | X | X | X | X |
| Feed attractant effect | | | | | | | | |
| Immediately after tableting | + | + | + | + | — | — | — | — |
| After being kept at 50° C. for 10 days | + | + | + | + | — | — | — | — |
| Insecticidal effect | | | | | | | | |
| Immediately after tableting | + | + | + | + | — | — | — | — |
| After being kept at 50° C. for 10 days | + | + | + | + | — | — | — | — |

Note:
*1Upper column, microencapsulated with polyurethane.
Lower column, non-microencapsulated.
*2Upper column, microencapsulated with porous silica.
Lower column, non-microencapsulated.

TABLE 3

| | (part(s) by weight) | | | | | |
|---|---|---|---|---|---|---|
| | Example | | | | | |
| | 14 | 15 | 16 | 17 | 18 | 19 |
| Component | | | | | | |
| Insecticide | | | | | | |
| Diazinon*2 | 1.0 | — | — | — | — | — |
| Chlorpyriphos*3 | — | 0.3 | — | — | — | — |
| Permethrin*2 | — | — | 0.1 | — | — | — |
| Cyphenothrin*2 | — | — | — | 0.05 | — | — |
| MPMC*2 | — | — | — | — | 0.6 | — |
| CPMC*2 | — | — | — | — | — | 0.8 |
| Crystalline cellulose | 25.0 | 60.0 | 20.0 | 25.0 | 45.0 | 35.0 |
| Saccharide | | | | | | |
| Black sugar | 25.00 | — | — | — | 40.0 | — |
| Brown sugar | — | 10.0 | — | 30.0 | — | — |
| Soft brown sugar | — | — | 20.0 | — | — | 20.0 |
| Starch | | | | | | |
| Corn starch | 49.2 | — | — | 44.34 | — | 31.58 |
| Potato starch | — | 24.55 | 59.9 | — | 11.3 | — |
| Additive | | | | | | |
| Dibutylhydrooxytoluene | — | 0.05 | — | 0.01 | — | — |
| Nordihydroguaiaretic acid | — | — | — | — | — | 0.02 |
| Dehydroacetic acid | — | 0.1 | — | — | 0.1 | 0.1 |
| Red pepper powder | 0.5 | — | — | 0.5 | — | 0.5 |
| Red No. 1 | Slight | — | — | Slight | Slight | — |
| Essential oil | | | | | | |
| Corn oil | — | 5.0 | — | — | 3.0 | — |
| Sesame oil | — | — | — | — | — | 2.0 |
| Chocolate flavor | 0.3 | — | — | 0.1 | — | — |
| Evaluation | | | | | | |
| Stability of active ingredient | O | O | O | O | O | O |

TABLE 3-continued

| | (part(s) by weight) Example | | | | | |
|---|---|---|---|---|---|---|
| | 14 | 15 | 16 | 17 | 18 | 19 |
| Feed attractant effect | | | | | | |
| Immediately after tableting | + | + | + | + | + | + |
| After being kept at 50° C. for 10 days | + | + | + | + | + | + |
| Insecticidal effect | | | | | | |
| Immediately after tableting | + | + | + | + | + | + |
| After being kept at 50° C. for 10 days | + | + | + | + | + | + |

Note:
*2microencapsulated with porous silica.
*3microencapsulated with gelatin.

It is understood from the above results that the tablets according to the invention are quite satisfactory in stability, feed attractant effect and insecticidal effect.

What is claimed is:

1. A bait composition for the control of noxious insects which comprises (a) at least one insecticide selected from the group consisting of organic phosphorous insecticides, carbamate insecticides and pyrethroid insecticides in a microencapsulated form, (b) cryatalline cellulose, (c) crop product powders and (d) a saccharide, wherein the components (a), (b), (c) and (d) are contained respectively in amounts of 0.05 to 5.0% by weight, 20.0 to 60.0% by weight, 11.3 to 79.0% by weight and 1.0 to 40.0% by weight based on the total weight of the composition wherein said composition is in a tablet form.

2. The composition according to claim 1, wherein the crop product powders are selected from the group consisting of potato starch, sweet potato starch, corn starch, wheat flour, rice powder and corn powder.

3. The composition according to claim 1, wherein the saccharide is selected from the group consisting of sucrose, glucose, fructose, lactose, black sugar, brown sugar and soft brown sugar.

4. The composition according to claim 1, which further comprises at least one additive and/or at least one auxiliary agent.

5. The composition according to claim 4, wherein the additive and the auxiliary agent are selected from the group consisting of an anti-oxidizing agent, a preservative, a mis-feed inhibitor, a flavoring agent and a feed attractant.

6. The composition according to claim 1, wherein the organic phosphorous insecticide is a member selected from the group consisting of calbinphos, chlorpyriphos, chlorpyriphosmethyl, cyanofenphos, cyanophos, diazinon, dichlorvos, fenitrothion, fenthion, malathion, naled, pirimiphosmethyl, prothiophos, pyridaphention, salithion, tetrachlorvinphos, trichlorfon, bromophos, and propetamphos.

7. The composition according to claim 1, wherein the carbamate insecticide is a member selected from the group consisting of BPMC, carbaryl, CPMC, ethiofencarb, MPMC, MTMC, promecarb, swep, and propoxur.

8. The composition according to claim 1, wherein the pyrethroid insecticide is a member selected from the group consisting of cypermethrin, cyphenothrin, deltamethrin, fenpropathrin, fenvalerate, kadethrin, permethrin, phenothrin, proparthrin, resmethrin, ethofenprox, cyflurthrin, alpha-methrin, tralomethrin, and fulcythrinate.

9. The composition according to claim 5, wherein the antioxidizing agent is a member selected from the group consisting of erythorbic acid, sodium erythorbate, dibutyl hydroxytoluene, dl-alphatocophelol, nordihydroguaiaretic acid, methylhydroxyanisole, propyl gallate, guaiac resin, and L-cysteine hydrochloride.

10. The composition according to claim 5, wherein the preservative is a member selected from the group consisting of benzoic acid, sodium benzoate, salicylic acid, diphenyl, sorbic acid, potassium sorbate, dehydroacetic acid, sodium dehydroacetate, isobutyl p-oxybenzoate, isopropyl p-oxybenzoate, ethyl p-oxybenzoate, butyl p-oxybenzoate, propyl p-oxybenzoate, calcium propionate, and sodium propionate.

11. The composition according to claim 5, wherein the mis-feed inhibitor is a member selected from the group consisting of red pepper powder, Amaranth, Amaranth aluminum lake, Erythrosine, Erythrosine aluminum lake, New Coccine, Phloxine, Rose Bengal, Acid Red, Tartrazine, Tartrazine aluminum lake, Sunset Yellow FCF, Sunset Yellow FCF aluminum lake, Fast Green FCF, Fast Green FCF aluminum lake, Brilliant Blue FCF, Brilliant Blue FCF aluminum lake, Indigo Carmine, Indigo Carmine aluminum lake, beta-carotene, copper and chlorophyll.

12. The composition according to claim 5, wherein the flavoring agent is a member selected from the group consisting of cheese flavor, butter flavor, peanut flavor, peach flavor, strawberry flavor, and milk flavor.

13. The composition according to claim 5, wherein the feed attractant is a member selected from the group consisting of soybean oil, rapeseed oil, sesame oil, cottonseed oil, wheat germ oil, corn oil, sunflower oil, palm oil, caster oil, and linseed oil.

* * * * *